United States Patent [19]

Wu

[11] Patent Number: 5,389,063
[45] Date of Patent: Feb. 14, 1995

[54] COLORFUL MASSAGING BALL STRUCTURE

[76] Inventor: Otto Wu, Room 918, 15 Fu Hsing N. Road, Taipei, Taiwan, Prov. of China

[21] Appl. No.: 142,129

[22] Filed: Oct. 28, 1993

[51] Int. Cl.$^6$ .................. A61H 15/00; A61H 7/00; A63F 9/06

[52] U.S. Cl. .................. 601/135; 601/131; 601/134; 273/153 S

[58] Field of Search ........ 600/9; 601/15, 19, 128–132; 273/153 S

[56] References Cited

U.S. PATENT DOCUMENTS

| | | | |
|---|---|---|---|
| 420,300 | 1/1890 | Hicks | 600/9 |
| 4,452,454 | 6/1984 | Gustafson | 273/153 S |
| 4,484,744 | 11/1984 | Gmünder | 273/153 S |
| 4,575,088 | 3/1986 | Peek | 273/153 S |
| 4,625,967 | 12/1986 | Yu | 273/153 S |
| 4,744,350 | 5/1988 | Sato | 601/15 X |
| 4,846,159 | 7/1989 | Anzai et al. | 601/128 |
| 4,889,340 | 12/1989 | Green | 273/153 S |
| 5,114,148 | 5/1992 | Lin | 273/153 S |
| 5,215,305 | 6/1993 | Hsun | 273/153 S |
| 5,308,066 | 5/1994 | Pataki | 273/153 S |

FOREIGN PATENT DOCUMENTS

| | | | |
|---|---|---|---|
| 0512928 | 11/1992 | European Pat. Off. | 273/153 S |
| 2549381 | 1/1985 | France | 273/153 S |
| 0673093 | 2/1990 | Switzerland | 273/153 S |
| 2088728 | 6/1982 | United Kingdom | 273/153 S |
| 8203792 | 11/1982 | WIPO | 273/153 S |

*Primary Examiner*—Robert A. Hafer
*Assistant Examiner*—Brian E. Hanlon
*Attorney, Agent, or Firm*—Morton J. Rosenberg; David I. Klein

[57] ABSTRACT

A colorful massaging ball structure having an upper and lower hemisphere is provided. A magnetic rod is provided within the center of the enclosure of the hemispheres to add to the therapeutic effects of the device. Along the surface of the hemisphere, a plurality of arch-shaped slide rails are provided having movable massaging element engaged thereon. The movable elements can be slidably moved along the slide rails. A plurality of protrusions on each movable element provides a stimulation of the vital points of the user's fingers.

1 Claim, 5 Drawing Sheets

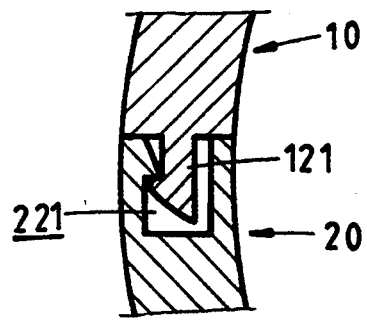
FIG.3
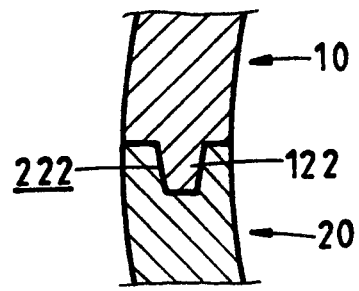
FIG.4
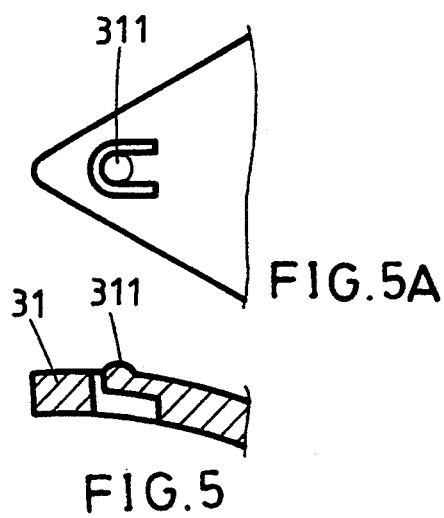
FIG.5A
FIG.5
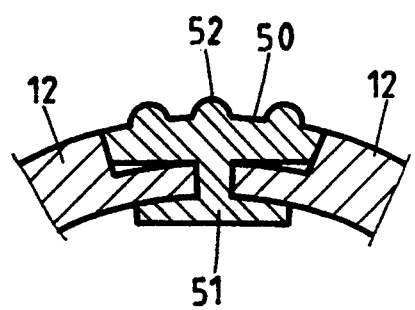
FIG.6

COLORFUL MASSAGING BALL STRUCTURE

BACKGROUND OF INVENTION

The present invention relates to a colorful massaging ball structure. In particular, the invention is directed to a massaging ball which can be used to stimulate the vital points of the fingers, and provides the therapeutic effect typically associated with a massaging device.

Presently, there are numerous types of massaging apparatus available on the market. For instance, massaging pads, massaging balls, massaging chairs, and massaging machines, etc. are all available. However, all these massaging devices make use of a knocking, compression and vibration process to stimulate the veins, arteries and vital points of the human body so as to achieve their therapeutic effect. Under the operation of the conventional type of massaging apparatus, the method of massaging is not effective, as the stimulated part is not self-activated. In other words, only a specific function of stimulation is contained for a specific type of massaging apparatus, and it does not provide for any additional functions, such as providing fun while practicing the massaging process.

SUMMARY OF THE INVENTION

It is an object of the present invention to provide a colorful massaging ball structure comprising an upper and lower hemisphere having a plurality of arch-shaped plates with protrusions on the surface thereof. The arch-shaped plates are slidably mounted and are slidable on the surface of the ball structure.

It is another object of the present invention to provide a colorful massaging ball structure which is used to massage the vital points of the fingers of the human body.

It is yet another object of the present invention to provide a colorful massaging ball structure which has a simple structure and is useful in massaging to provide a therapeutic effect to the muscles of the human body.

Still other objects of the present invention will become readily apparent to those skilled in this art from the following description wherein there is shown and described a preferred embodiment of this invention simply by way of illustration of one of the modes best suited to carry out the invention.

BRIEF DESCRIPTION OF THE DRAWINGS

The accompanying drawings incorporated in and forming a part of the specification, illustrate several aspects of the present invention, and together with the description serve to explain the invention. In the drawings:

FIG. 3 is an enlarged partial sectional view, showing the dovetail of the upper hemisphere and the engaging slot of the lower hemisphere, in accordance with the present invention;

FIG. 4 is an enlarged partial sectional view, showing the adjusting peg of the upper hemisphere and the adjusting hole of the lower hemisphere, in accordance with the present invention;

FIG. 5 is an enlarged partial sectional view showing the engaging block at the terminal end element, in accordance with the present invention;

FIG. 5A is a partial plan view showing the engaging block, in accordance with the present invention;

FIG. 6 is an enlarged partial sectional view showing the structure of the movable massaging element and the slidable rail used in the upper and lower hemisphere structures of the present invention;

DETAILED DESCRIPTION OF THE PREFERRED EMBODIMENT

Figure 1:
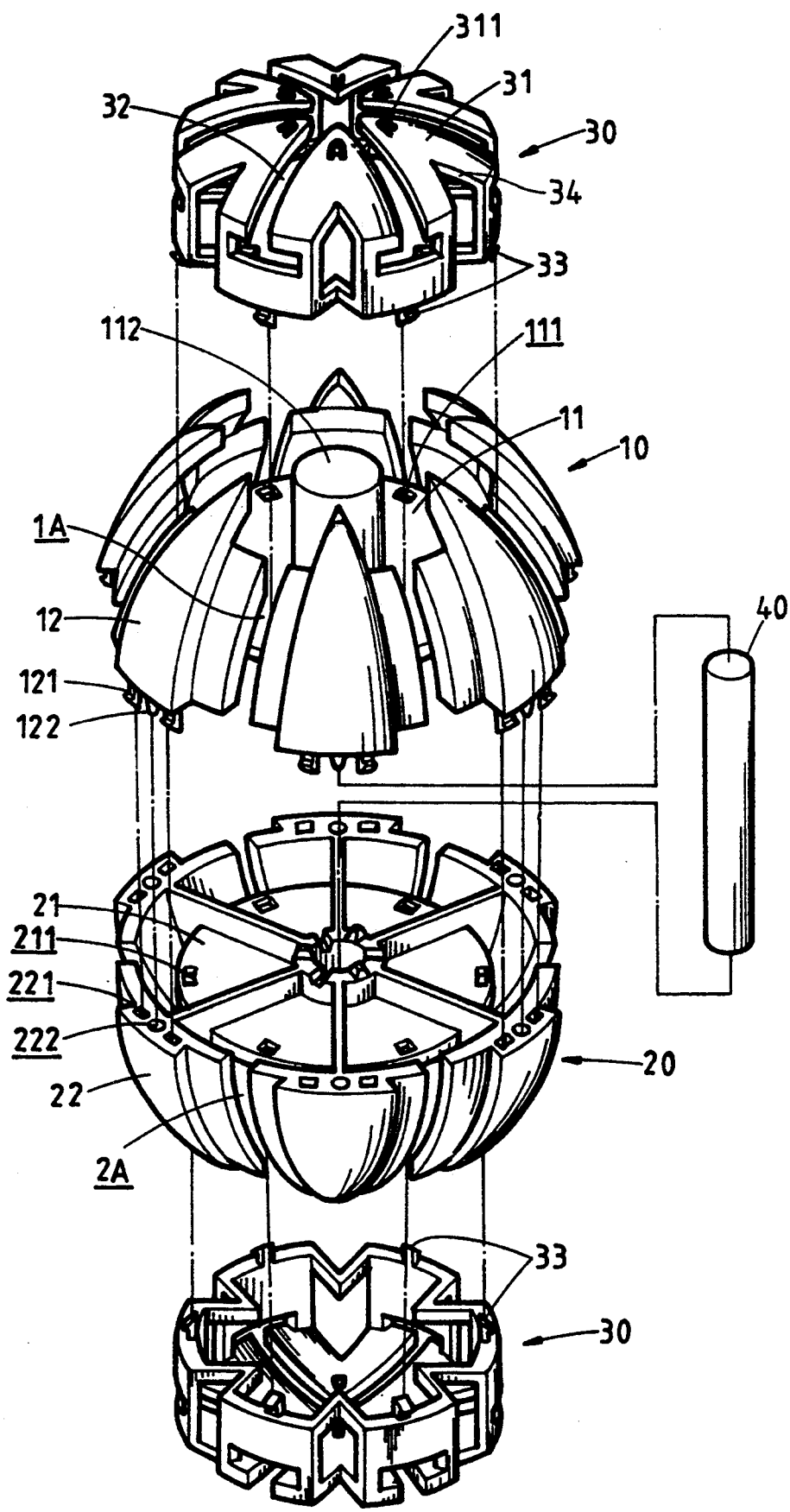
FIG. 1 is an exploded view of the massaging ball structure in accordance with the present invention.

Referring to FIGS. 1-6, there is shown, the massaging ball 100. The massaging ball 100 comprises an upper hemisphere 10 and a lower hemisphere 20. The center region of the upper hemisphere of the ball 100 is provided with a plate 11 having a plurality of through holes 111 formed along the peripheral edge of plate 11. The center region of the plate 11 is provided with a hollow cylindrical body 112 having the bottom end formed with a sawtooth-like structure. Surrounding the plate 11 there are formed a plurality of arch-shaped triangular segments 12 disposed in radially spaced relation such that the top end of the upper hemisphere 10 forms a circular opening. Between each adjacent pair of triangular segments 12 there are formed a slotted slide rail 1A. The bottom ends of each of the triangular segments 12 are provided with an alignment rod 122 disposed between two dovetails 121.

Similar to the upper hemisphere 10, the lower hemisphere 20 is provided with a plate 21, engaging holes 211, a center hollow cylindrical body 212 and a plurality of arch-shaped triangular segments 22. At the bottom end of the lower hemisphere 20, a circular opening is formed, as is similarly provided on the top of the upper hemisphere 10. Between adjacent pairs of the radially spaced triangular segments 22, there are likewise formed respective slotted slide rails 2A. At the top end face of each individual triangular segment 22 there is formed an engaging slot 221 corresponding to each of the dovetails 121 of a respective upper hemisphere triangular segment 12 for the engagement of the upper hemisphere 10 and the lower hemisphere 20 (as shown in FIG. 3). Disposed between the two slots 221 of each triangular segment 22 there is formed an adjusting hole 222 corresponding to the alignment rod 122 of a respective upper hemisphere triangular segment for alignment of the engagement of the upper hemisphere 10 and the lower hemisphere 20 (as shown in FIG. 4). The upper and lower hemisphere 10 and 20 are combined by means of the sawtooth-like structure at the top end of the hollow cylindrical body 212, such that the engagement of the upper hemisphere 10 and the lower hemisphere 20 is firm and secure.

In addition, two end elements 30, which may be formed of a metallic material, fill the respective circular openings at the bottom end of the lower hemisphere 20 and the top end of the upper hemisphere 10. The top portion of each end portion is provided with triangular segments 31, each having a notch 34 corresponding to the apex of a respective triangular segment 12, 22. Between each adjacent end portion triangular segment there is formed a slotted opening 32 which correspondingly aligns with respective slide rails 1A, 2A of the upper hemisphere 10 or lower hemisphere 20. Each notch 34 is centrally disposed at the end face of the respective triangular segment 31. Each of those segments are provided with an elastic engaging block 311, as shown in FIGS. 5 and 5A, and at the circumferential edge of the bottom end thereof, dovetails 33 corresponding to a respective engaging hole 111, 211 of the upper hemisphere 10 or lower hemisphere 20 are provided for the engagement of a respective end portion 30 to the top portion of the upper hemisphere 10 and the bottom portion of the lower hemisphere 20. Such engagement providing for a respective slide rail 1A, 2A of the upper hemisphere 10 or the lower hemisphere 20 being in open communication with the slotted opening 32.

Figure 2:
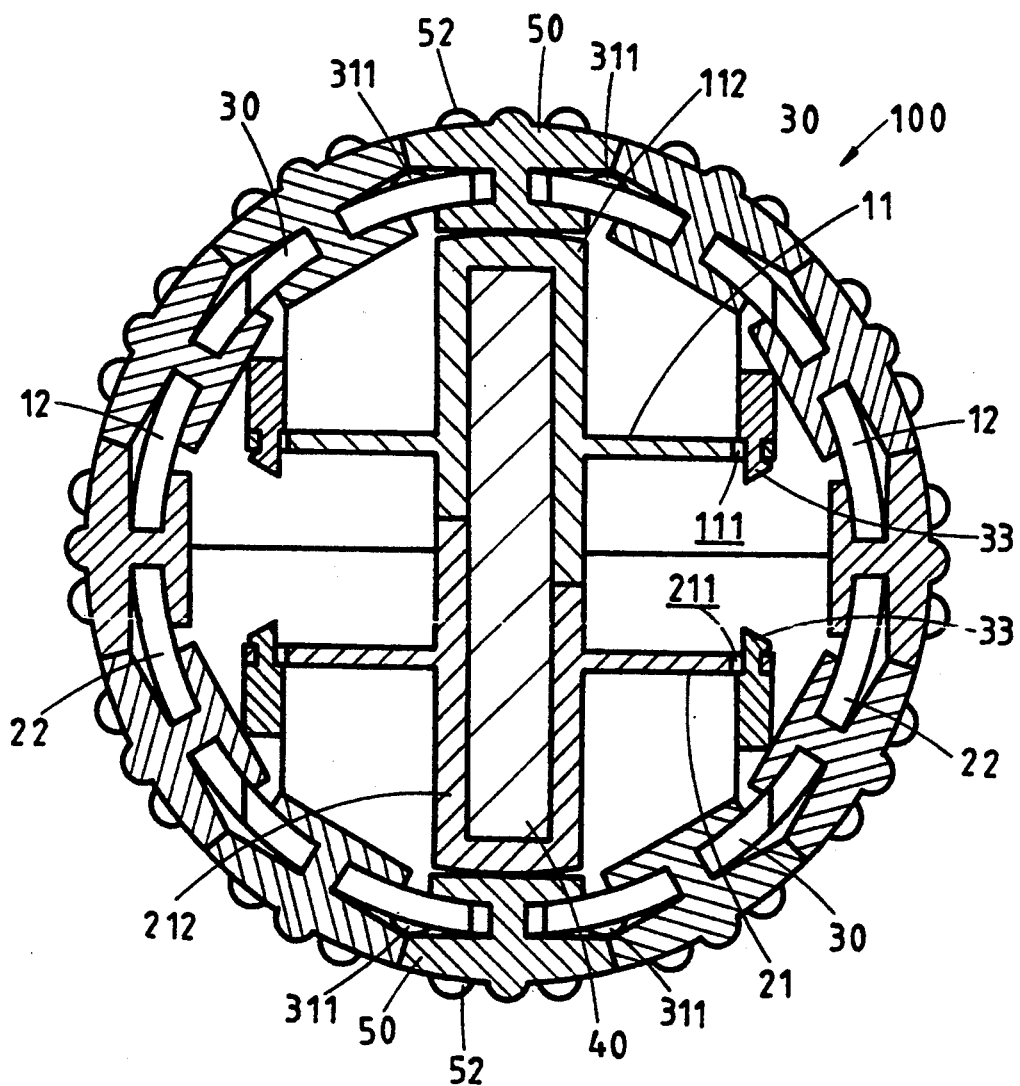
FIG. 2 is a sectional view of the ball structure in accordance with the present invention.

A magnetic rod 40 having a cylindrical contour is mounted within the hollow cylindrical bodies 112, 212, and extending therebetween. A plurality of movable massaging elements 50 are provided having a size and degree curvature corresponding to the slide rail 1A and 2A of the upper hemisphere 10 and lower hemisphere 20, respectively. At the lower end of each of the movable massaging elements 50 there is formed an engaging block 51 corresponding to the underside of the slide rails 1A and 2A for sliding engagement therewith, as shown in FIG. 6. At the center region, the intersection of the slotted openings 32 of the end portion 3, the movable massaging elements 50 are prevented from simply loosening by the biasing action of the elastic engaging blocks 311, as shown in FIGS. 2 and 7.

Additionally, the movable massaging elements 50 of the individual slide rails 1A and 2A are provided in different colors. A plurality of protrusions 52 are formed on the surface of each movable massaging element 50. The movable massaging elements 50 are disposed on the slide rails 1A and 2A and engaged therewith such that the upper hemisphere 10 and lower hemisphere 20 are combined to form a ball structure. The movable massaging elements 50 can freely move from one slotted opening to a respective slide rail 1A, 2A or from one respective slide rail 1A, 2A, via slotted opening 32, to the center region of an end portion 30.

Figure 7:
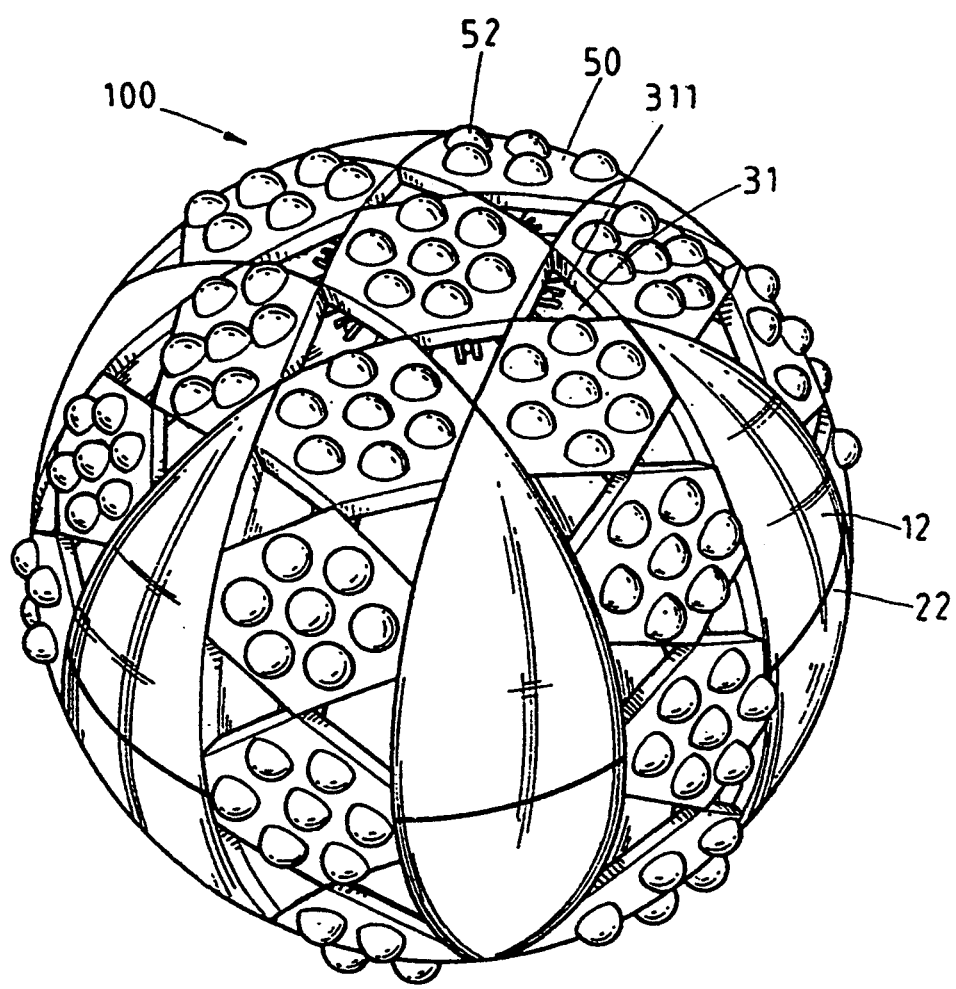
FIG. 7 is a perspective view of the massaging ball structure in accordance with the present invention; and, FIG. 8 is a perspective view of preferred embodiment of the present invention illustrating its use.
Figure 8:
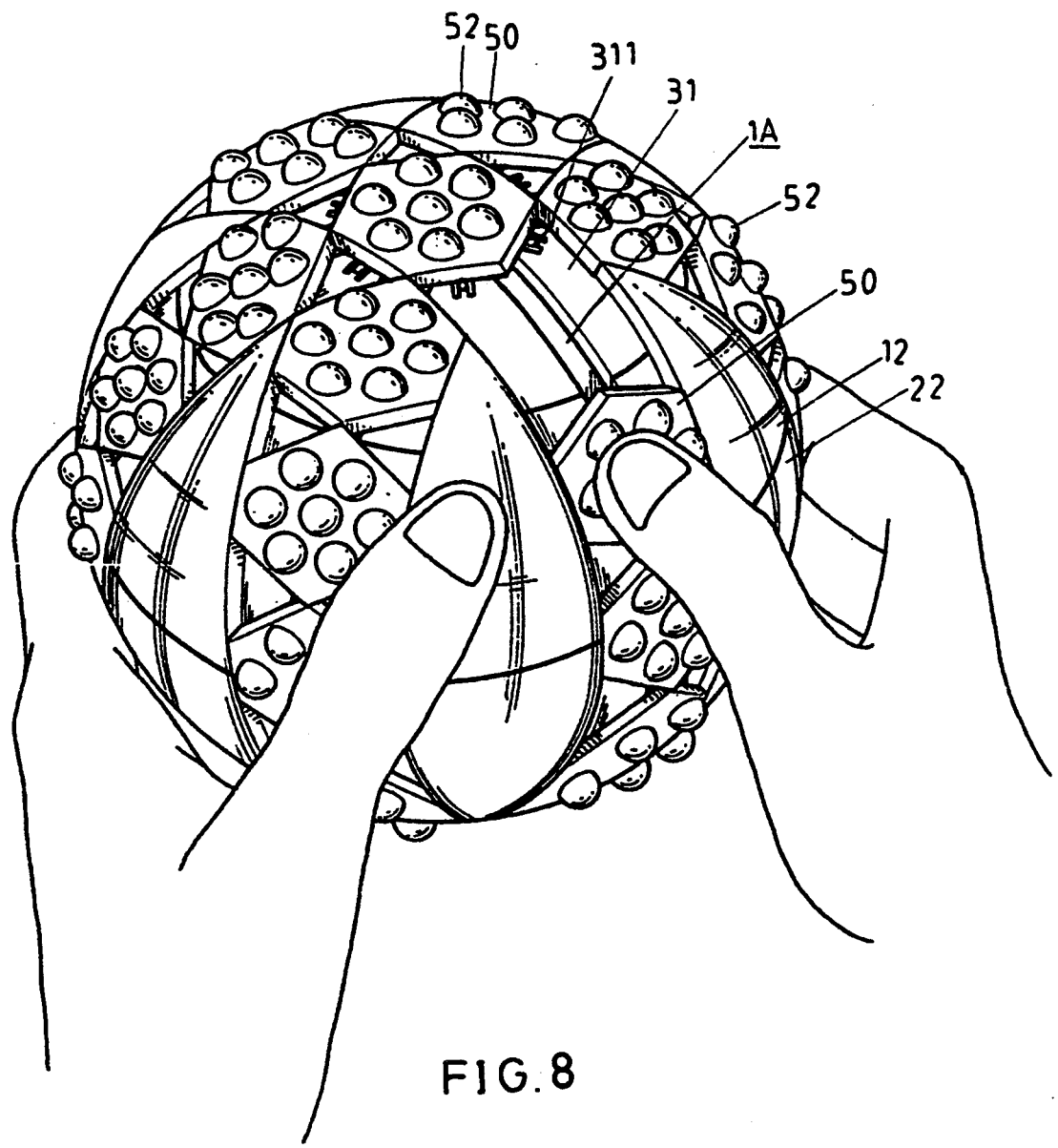

Referring to FIGS. 7 and 8, there is shown, the assembled construction of a massaging ball structure 100. In operation, one or at least one, of the movable massaging elements 50 are arranged such that it can be moved along the slide rail 1A, 2A by a user's finger, and then supplement the space left thereby with another movable element 50 along the slide rail 1A, 2A. The vital points, the arteries and veins of the user's fingers will be massaged by the protrusions 52 provided on the surface of the element 50 as the elements 50 are displaced. This massaging provides a therapeutic effect due to the stimulation of those vital points which occurs in combination with the muscle movement of the finger. A self-activated massaging effect is thereby produced. The further combination of the magnetic rod 40 within the ball structure 100 will produce an additional therapeutic effect. The ball structure 100, being provided with various color massaging elements 50 also presents an attractive product having practical efficacy.

In this disclosure, there is shown and described only the preferred embodiment of the invention, but, as aforementioned, it is to be understood that the invention is capable of use in various other combinations and is capable of changes and modifications within the scope of the inventive concept as expressed herein.

I claim:

1. A ball structure for massaging a user's fingers to provide a therapeutic effect, comprising:

an upper hemispherical member having a first circular plate formed therein, said upper hemispherical member having a first centrally disposed hollow cylindrical body portion extending from said first circular plate along a polar axis of said upper hemispherical member, said first hollow cylindrical body portion having an open proximal end adjacent a bottom surface of said first circular plate and a closed distal end, said open end of said first hollow cylindrical body portion having a sawtooth edge surface formed thereon, said upper hemispherical member further having an outer surface defined by a plurality of first triangularly shaped segment portions disposed in radially spaced relation and a plurality of first slide rail portions disposed between each adjacent pair of said first triangularly shaped segment portions, each of said first triangularly shaped segment portions extending to an apex disposed at a polar portion of said upper hemispherical member to form a first opening thereat having a substantially circular contour;

a lower hemispherical member having a second circular plate formed therein, said lower hemispherical member having a centrally disposed second hollow cylindrical body portion extending from said second circular plate along a polar axis of said lower hemispherical member, said second hollow cylindrical body portion having an open proximal end adjacent a bottom surface of said second circular plate and a closed distal end, said open end of said second hollow cylindrical body portion having a sawtooth edge surface formed thereon for engagement with said sawtooth edge surface of said first hollow cylindrical body portion, said lower hemispherical member further having an outer surface defined by a plurality of second triangularly shaped segment portions disposed in radially spaced relation and a plurality of second slide rail portions disposed between each adjacent pair of said second triangularly shaped segment portions, each of said second slide rail portions being disposed in corresponding alignment with a respective one of said first slide rail portions, each of said second triangularly shaped segment portions extending to an apex disposed at a polar portion of said lower hemispherical member to form a second opening thereat having a substantially circular contour;

means for lockingly engaging said upper hemispherical member with said lower hemispherical member;

a pair of end members, each of said pair of end members being secured within a respective one of said first and second polar openings, each of said pair of end members having an outer surface defined by a plurality of third triangularly shaped segment portions and a plurality of slotted openings formed between adjacent pairs of said plurality of said third triangularly shaped segment portions, each of said plurality of slotted openings being disposed in corresponding alignment with a respective one of said first and second slide rail portions, each of said third triangularly shaped segment portions having an elastic engagement tab portion formed therein adjacent an apex of said third triangularly shaped segment portions;

a plurality of massaging elements, each of said massaging elements having an upper surface and a lower surface, each of said massaging elements having an engagement block portion formed on said lower surface for sliding engagement with a respective first slide rail portion, second slide rail portion and said end member slotted opening, each of said plurality of massaging elements having a plurality of protrusions extending from said upper surface thereof for massaging a user's fingers as said massaging element is slidingly displaced, said third triangularly shaped segment portion elastic engagement tab portions providing biased releasable engagement of a respective one of said massaging elements at an intersection of said end member slotted openings; and, a cylindrically shaped magnet having a first end enclosed within said first hollow cylindrical body portion and a second end enclosed within said second hollow cylindrical body portion for providing an additional therapeutic effect to the user's fingers.

* * * * *